(12) United States Patent
Brenk et al.

(10) Patent No.: US 10,994,272 B2
(45) Date of Patent: May 4, 2021

(54) CARDIAC BIOMARKER ASSAY CARTRIDGE OR CARD

(71) Applicant: Zepto Life Technology, LLC, St. Paul, MN (US)

(72) Inventors: Victor Reed Brenk, Minneapolis, MN (US); Todd Michael Klein, Wayzata, MN (US); Wei Wang, St. Paul, MN (US)

(73) Assignee: ZEPTO LIFE TECHNOLOGY, LLC, St. Paul, MN (US)

( * ) Notice: Subject to any disclaimer, the term of this patent is extended or adjusted under 35 U.S.C. 154(b) by 73 days.

(21) Appl. No.: 15/923,223

(22) Filed: Mar. 16, 2018

(65) Prior Publication Data

US 2019/0283025 A1 Sep. 19, 2019

(51) Int. Cl.
*B01F 5/06* (2006.01)
*B01F 13/00* (2006.01)
*B01L 3/00* (2006.01)
*G01N 33/50* (2006.01)

(52) U.S. Cl.
CPC ... *B01L 3/502738* (2013.01); *B01L 3/502753* (2013.01); *G01N 33/5005* (2013.01); *B01L 2200/04* (2013.01); *B01L 2200/0605* (2013.01); *B01L 2200/0684* (2013.01); *B01L 2200/10* (2013.01); *B01L 2300/0681* (2013.01); *B01L 2300/0816* (2013.01); *B01L 2300/123* (2013.01); *B01L 2400/06* (2013.01); *B01L 2400/0655* (2013.01)

(58) Field of Classification Search
USPC .......... 422/501–505, 513, 554, 48; 436/180; 700/274
See application file for complete search history.

(56) References Cited

U.S. PATENT DOCUMENTS

2017/0260567 A1* 9/2017 Selden .............. B01L 3/502707
2017/0312751 A1* 11/2017 Glezer .................. B01L 3/5027

OTHER PUBLICATIONS

International Search Report and Written Opinion dated May 8, 2019 in International Application PCT/US2019/021837.
International Preliminary Report on Patentability dated Oct. 1, 2020 in International Application PCT/US2019/021837.

* cited by examiner

*Primary Examiner* — Dean Kwak
(74) *Attorney, Agent, or Firm* — Pillsbury Winthrop Shaw Pittman LLP (57) ABSTRACT

An assay cartridge for mixing a test sample and reagent for diagnostic purposes, and method of using the same. The assay cartridge includes a housing, an injection port for receiving the test sample (whole blood), a filtration membrane for separating plasma from the sample, a section for receipt of reagent, and one or more sets of valves provided in the housing. Each valve is configured for movement between an open position and a closed position. Metering chambers are provided in the housing for receiving separated plasma and the reagent therein. A port is fluidly connected to each metering chamber and uses to draw air from or deliver pressurized fluid into the housing. Mixing channels are provided in the housing and selectively connected to the metering chambers for mixing the separated plasma and reagent into a substantially homogeneous mixture. The homogeneous mixture is delivered out of the housing through output ports.

13 Claims, 9 Drawing Sheets

CARDIAC BIOMARKER ASSAY CARTRIDGE OR CARD

BACKGROUND

Field

The present disclosure is generally related to an assay cartridge used for diagnostic purposes, and its method of use.

Description of Related Art

Generally, it is common to use a card to test for a single biomarker in a blood sample. Adding a blood sample to known cards generally relies simply on lateral flow of the blood sample into the card before a reading is performed. Also, current assay systems in the medical market generally rely on capillary separation of a whole blood sample, which generally limits detection methodology to optical analysis or visual testing.

Furthermore, known systems are unable to analyze large numbers of different biomarkers in a singular patient sample, and are instead forced to design multiple cards for each biomarker.

SUMMARY

It is an aspect of this disclosure to provide an assay cartridge for mixing a test sample and reagent for diagnostic purposes, the assay cartridge including: a housing; an injection port for receiving the test sample, the test sample comprising whole blood; a filtration membrane provided in the housing for separating plasma from the test sample; a reagent injection section for receipt of the reagent; a first set of valves provided in the housing comprising at least a first valve and a second valve, each valve configured for movement between an open position and a closed position; at least one metering chamber provided in the housing for receiving the separated plasma and the reagent therein; at least one port fluidly connected to the metering chamber, the port configured to selectively draw and deliver pressurized fluid into the housing; at least one mixing channel provided in the housing for mixing the separated plasma and reagent into a substantially homogeneous mixture, the mixing channel being selectively connected to the at least one metering chamber based on positioning of the first and second valves for receipt of the separated plasma and reagent from the metering chamber; and at least one output port for delivering the homogeneous mixture from the mixing channel and out of the housing.

Another aspect provides a method of using a cartridge to mix a test sample and reagent material, the cartridge comprising a housing configured to receive the test sample and the reagent, the test sample being injected into an injection port of the housing for filtering by a filtration membrane in the housing to separate plasma from the test sample, the housing including: a first set of valves provided therein comprising at least a first valve and a second valve, each valve configured for movement between an open position and a closed position, at least one metering chamber, at least one port, at least one mixing channel, and at least one output port; the method comprising: controlling at least a first valve and a second valve by placing the first valve in an open position and the second valve into a closed position; delivering plasma separated from the injected test sample and the reagent into the metering chamber; then, delivering the plasma and the reagent from the at least one metering chamber to the at least one mixing channel via application of pressurized fluid into the housing via the at least one port; mixing the plasma and reagent into a substantially homogeneous mixture using at least one mixing channel; and delivering the homogeneous mixture from the mixing channel and out of the housing via the at least one output port.

Other aspects and features of this disclosure will become apparent from the following detailed description, the accompanying drawings, and the appended claims.

DETAILED DESCRIPTION OF THE PREFERRED EMBODIMENT(S)

Disclosed herein is a microfluidics cartridge or card that is used in conjunction with a device or system having a sensor configured to detect multiple features from a mixture received from the cartridge. In one embodiment, the disclosed cartridge may be used in conjunction with a device or system having a detection methodology (GMR) and is configured for multiplexing and identifying multiple biomarkers from a single patient blood sample (instead of being limited to a single biomarker). In accordance with an embodiment, the herein described cartridge receives a patient blood sample and is configured to mix it with a reagent such that the sensor may analyze multiple (e.g., five (5)) targeted biomarkers associated with cardiac distress in a single step. This device and technology therefore offer users a more comprehensive analysis of the sample, without being limited to a single reading or single biomarker, thus allowing for a more precise diagnosis to be made.

FIGS. 1-4 illustrate features and structural elements of the assay cartridge 100, which is also simply referred to as a "cartridge" herethroughout. The cartridge 100 or card may be used for diagnostic and analysis purposes, e.g., such as a biological sample analyzer in the form of a disposable card designed for a one time use. The structural features of the cartridge 100 allow for control of fluid movements and handling volumes of fluids and flow through the cartridge 100. The cartridge 100 is formed of a body or a housing that has a top surface 18 and a bottom surface 20 (shown in FIG. 4). The housing may be formed using parts that are laser cut to form inlets, channels, valve areas, etc. and sandwiched and connected/sealed together, in accordance with an embodiment. In another embodiment, one or more layers of the housing may be laser cut, laminated, molded, etc. or formed from a combination of processes. The method of forming the housing of the cartridge 100 is not intended to be limiting. For illustrative purposes herein, some of the Figures include a depiction of layers to show positioning of parts of the cartridge 100 relative to one another. Such illustrations are provided to show exemplary depths or placement of the features (channels, valves, etc.) within the housing or body of the cartridge, without being limiting.

Figure 1:
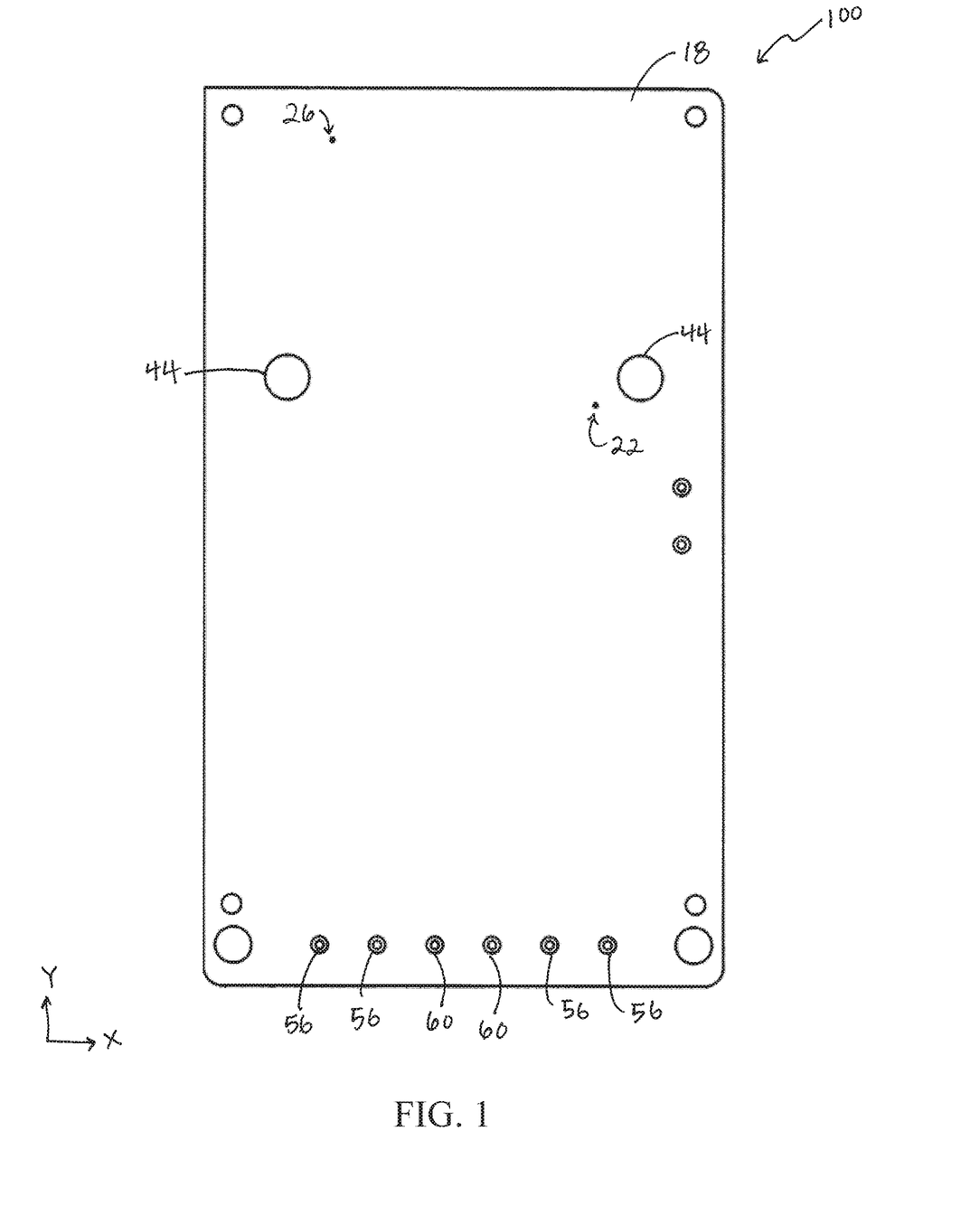
FIG. 1 is a top or overhead view of an assay cartridge, in accordance with an embodiment of this disclosure, illustrating features thereof.

The cartridge 100 generally includes receiving, input, and mixing areas or zones for processing a blood sample, generally represented in FIG. 1. For example, the cartridge 100 may include a sample injection area 10, a valve array and control zone 12, a mixing zone 14, and a second control and delivery zone 16. The structural features associated with these zones or areas are further described below with reference to FIGS. 2-5. These zones are not intended to be limiting in any way based on the illustrated figures and/or the features described with reference thereto. Rather, they are provided to generally represent features and functions associated with parts of the cartridge 100 itself. One of ordinary skill in the art will understand that one or more parts may be moved to or associated with an another zone or area, positioned at different depths or relative to other features, and that such zones need not be defined or predefined in the cartridge in any way.

Figure 2:
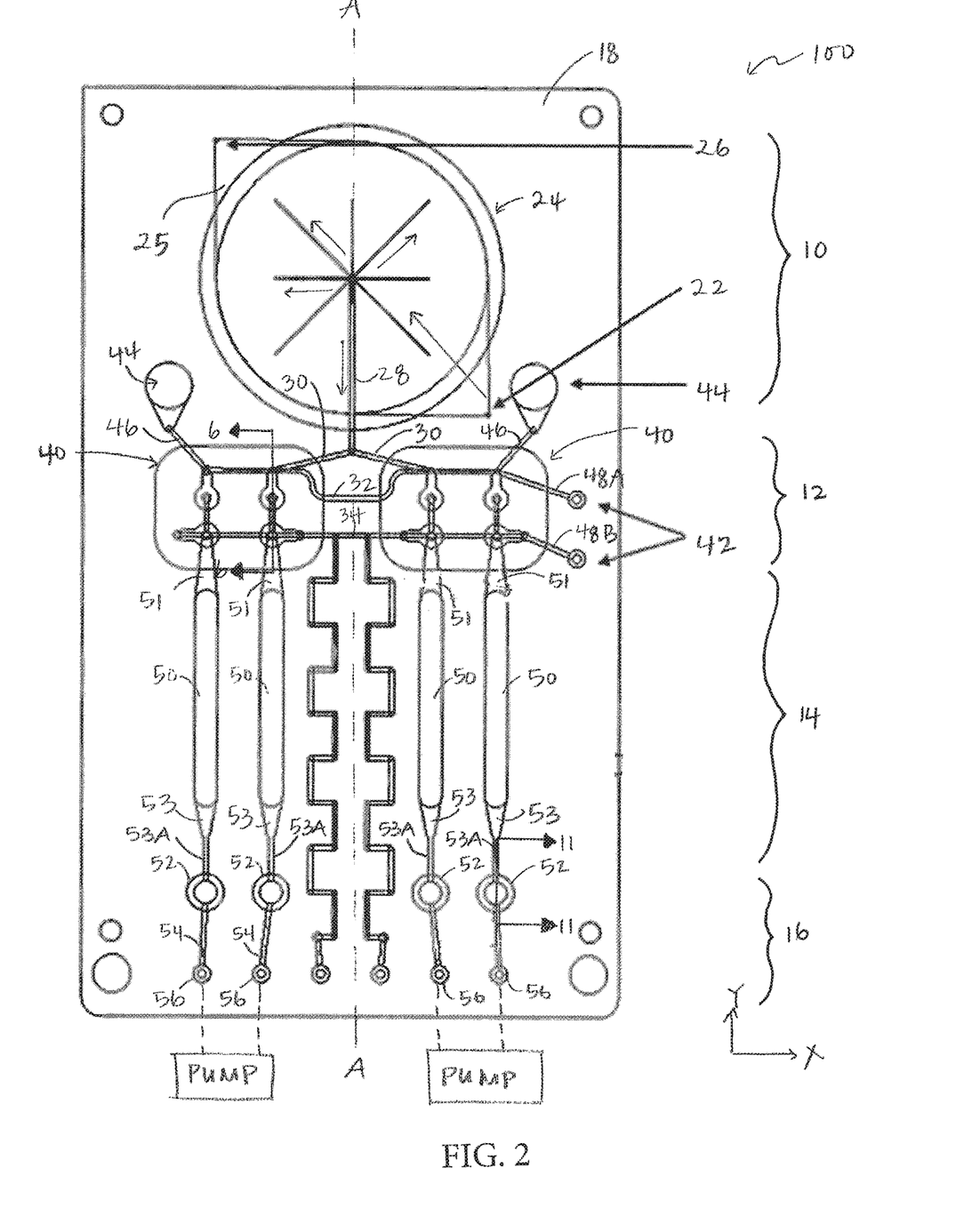
FIGS. 2 and 3 are top or overhead views of the cartridge of FIG. 1, each illustrating features provided in a housing or body of the cartridge, in accordance with an embodiment therein.

Referring now to FIG. 2, provided in the sample injection area 10 of the cartridge 100 are an injection port 22, blood filtration membrane 24 or filter, and vent port 26, for example. The injection port 22 is configured to receive a test sample, i.e., whole blood. The injection port 22 may include a small opening provided in the top surface 18 of the housing that extends vertically (downwardly) at a depth into the housing and through to the blood filtration membrane 24. In the exemplary illustrated embodiment, the injection port 22 is shown on a lower, right side near the membrane 24. The blood filtration membrane 24 is provided or sandwiched at a depth between the top surface 18 and bottom surface 20 of the housing. In the illustrated embodiment, the blood filtration membrane 24 depicted as being generally circular; however, the area or shape of the membrane 24 is not intended to be limited. As generally understood by one of skill in the art, the blood filtration membrane 24 is formed from a material configured to receive a whole blood sample and separate plasma from that sample. The blood filtration membrane 24 may be formed from an asymmetric filter material, for example. Such a material may have an increasing smaller pore size on its underside such that the membrane 24 is used to remove red blood cells and other large biological materials from the patient sample (whole blood) injected into the injection port 22.

A patient test sample (i.e., whole blood) is loaded, introduced, or injected (e.g., using a pipette or needle) into the small opening of injection port 22. The blood sample is configured to spread laterally through and across the blood filtration membrane 24 to purify and separate components of the injected whole blood sample, i.e., to yield plasma. The separated plasma may settle into a bottom portion or receiving area 25 (see FIGS. 2 and 4) in the cartridge 100, e.g., provided adjacent to or below (in the vertical direction, i.e., direction of depth or height, in the Z-direction) the filtration membrane 24, for example. More specifically, the loaded blood sample will wick across the filtration membrane 24—as represented by the lines therein—and up or diagonally to a side opposite the injection port 22, where the vent port 26 may be positioned or provided. Specifically, the illustrated lines in the filtration membrane 24 as shown in FIG. 2, for example, represent a structural, directional feature, such as channels, that are used to direct an injected whole blood sample to spread across membrane 24. Vent port 26 is an opening in the housing that extends vertically a depth between the area of the blood filtration membrane 24 and the top surface 18 of the cartridge 100. In an embodiment, the depth of the vent port 26 extends from the receiving area 25 to the top surface 18. Vent port 26 is open to the atmosphere and configured to vent air from the housing. Vent port 26 may be similar in size to the opening of injection port 22. The vent port 26 extends down into same plane as the membrane 24. This vent port 26 allows pressure to be vented or released from inside the cartridge (e.g., from the membrane 24 and/or receiving area 25) and out to the atmosphere; e.g., as the blood test sample is injected and wicked in the membrane 24, it separates the plasma and any air in this area is pushed out through vent port 26. In the exemplary illustrated embodiment, the vent port 26 is shown on an upper, left side near the membrane 24.

In accordance with an embodiment, vent port 26 may be positioned relatively opposite (180 degrees) to the injection port 22. In another embodiment, the vent port 26 and injection port 22 may be positioned closer together, or on a same side of the cartridge. In an embodiment, a channel, guide, or other portion may be provided in a layer of the cartridge that routes the channels around the membrane 24, for example. In one embodiment, the location of the injection port 22 and vent port 26 may be switched or rotated to another location around the filtration membrane 24. For example, referring to the exemplary illustrated embodiment as shown in FIGS. 1 and 2, the injection port 22 and vent port 26 locations may be switched. In another embodiment, the ports 22, 26 may be positioned along another line, e.g., a vertical line, a horizontal line, or angled line, across/through and relative to the membrane 24. Accordingly, the illustrated locations of the ports 22, 26 is not meant to be limiting.

From this sample injection area, the separated plasma within receiving area 25 is designed for use and mixing with a reagent. In the illustrated cartridge 100, the valve array and control zone 12, mixing zone 14, and second control and delivery zone 16 have features that are similar on either side (left and right) of a longitudinal centerline A-A (provided in the Y-direction) when viewed overhead (see FIG. 2), and thus are mirror images of each other. Accordingly, the cartridge 100 provides assay areas that are split and arranged in a parallel manner, allowing multiple assays at one time. In the Figures, similar reference numbers are used to represent features provided on both sides (i.e., left and right) of the cartridge 100. As will be further evident based on the description below, this structural arrangement on the cartridge 100 allows for better mixing of the plasma and reagent along with use of control mechanisms, thereby resulting in better functioning of the cartridge and thus higher assay specificity.

In accordance with an embodiment, the mechanisms used to control fluid mobility and mixing in the cartridge 100 are a series of valves provided in the valve and control zone 12 as well as ports in the second control and delivery zone 16. For example, plasma that is separated from a blood sample using the filtration membrane 24 in the receiving zone 25 may travel through a sample delivery channel 28 that extends from the receiving zone 25 (in this case, from a center, bottom portion thereof) via controlling such valves and ports using a controller and/or pump(s) connected to the cartridge 100, in accordance with one embodiment.

It should be noted that although a single sample delivery channel 28 is shown in the Figures, it is envisioned that two or more sample delivery channels 28 may be provided in the cartridge 100. For example, in an embodiment, two sample delivery channels 28 may extend between the receiving zone 25 and at least one of the valve array zones 40.

A series of valves may be provided in zones 40 and/or the valve and control zone 12. In an embodiment, a first set of valves is provided in the housing and includes a first valve and a second valve that are each configured for movement between an open position and a closed position. In one embodiment, a second set of valves is also provided in the housing, each valve being configured for movement between an open position and a closed position. The valves may be separated into valve array zones 40 provided on either side of the longitudinal centerline A-A of the cartridge housing and provided adjacent to or relatively below the filtration membrane 24 (relative to and along the centerline). In another embodiment, the valves may be provided on the same side of a longitudinal axis or centerline A-A of the housing.

In one embodiment, each valve array zone 40 may include or be formed from an elastomeric material 21, as shown in FIG. 1. As illustrated in the exemplary illustrated embodiment, the location of the elastomeric material 21 is represented by generally rounded rectangle section provided below the top surface 18 at a depth of the cartridge 100, at each valve array zone 40, for example. As described in greater detail later, the elastomeric material 21 is placed within the housing or body of the cartridge such that valves that are formed in layers or within the body of the cartridge. The elastomeric material 21 may include pockets and/or elastomeric deflection portions that are/act as the valves, which are aligned with interior channels within the cartridge. Movement of the deflection portions via positive pressure (e.g., pressurized air) between open and closed positions allows fluid (plasma, reagent) to move within the channels and housing parts, as described below.

The valves (i.e., elastomeric deflection portions) in the valve and control zone 12 may be selectively controlled to allow for selective delivery of the separated plasma from the blood sample and/or a reagent for mixing with the plasma to fluid metering chamber(s) 50 that may be provided in the mixing zone 14, for example. As detailed later, controller(s) and/or pump(s) that are connected to the cartridge 100 may be activated to control a position of the valves in the elastomeric materials 21/zones 40 and/or to apply positive and/or negative pressure (suction or vacuum) to the cartridge 100 such that, depending on the positioning of the valves, the fluids (plasma and/or reagent) move within and throughout channels provided in the cartridge 100. To move and deliver separated plasma into the metering chambers 50, the sample delivery channel 28 connects to branch portions 30. In one embodiment, two branch portions 30 are provided, each of which extends one of the valve array zones 40 (on either side of the centerline A-A), for example. Also connected to valve array zones 40 via delivery channels 46 are reagent injection sections 44. The reagent injection section 44 is designed to receive a reagent therein. The reagent injection sections 44 may be provided in the sample injection area 10, in the valve arrange and control zone 12, or partially in both, and thus their location is not intended to be limiting. In one embodiment, these sections 44 are provided in the housing of the cartridge 100 in the form of substantially rounded or circular well that receives and contains a volume reagent solution therein. The reagent solution may be metered from each of the sections 44 through delivery channels 46 via activating valves/controllers, such that it is combined with the separated plasma from the blood sample, described later below. A volume of reagent solution may be injected into, pre-loaded, or stored in the reagent injection sections 44 in the cartridge 100. In one embodiment, the reagent may be stored in the sections 44 of the cartridge 100 using a blister pack configuration, i.e., the reagent is contained in the cartridge and a seal is broken when testing of a sample takes place. In another embodiment, the reagent may be injected into the sections 44 and temporarily stored in the well/section until the valves/controllers are activated. In addition to selectively moving plasma, then, the valves in the each zone 40 may further control delivery and mobility of the reagent in the cartridge 100, i.e., into the fluid metering chambers 50.

The reagent or reagent solution may be one including magnetic nanoparticles to label target proteins. Generally, the reagent or reagent solution is configured to include an antibody that causes a mechanical reaction. Such types of reagents are known by one of ordinary skill in the art and thus not listed here.

The fluid metering chambers 50 are positioned beneath (in the Y-direction) and connected to channels in the zones 40 (these channels are described in greater detail below with respect to FIG. 5). As shown in FIG. 2, each fluid metering chamber 50 extends between the valve array zone 40 and a gas permeable membrane 52 which is generally located in the second delivery and control zone 16. Each of the chambers 50 (four are shown here) may be positioned at a depth within the housing, between the top and bottom surfaces 18 and 20, and in a manner such that they are parallel to one another in a lateral direction of the housing and extend a length in the longitudinal direction relative to the centerline A-A. Each chamber 50 is sized to receive metered fluids—i.e., a volume of separated plasma (blood) sample and a volume of reagent—therein, such that they may be mixed and used for biomarker sensing. As described in greater detail below, an open state for some of the valves allows for both the patient (plasma) sample and reagent(s) to separately be pulled into the fluid metering chambers 50 until the fluid(s) reach the gas permeable membranes 52. In accordance with an embodiment, the structural design of the channels in the cartridge 100 and valves allows the two fluids to be forced into the mixing region in a 1:1 ratio, when used along with a controller and/or pump. Each chamber 50 may be further configured to output the received fluids.

Figure 11:
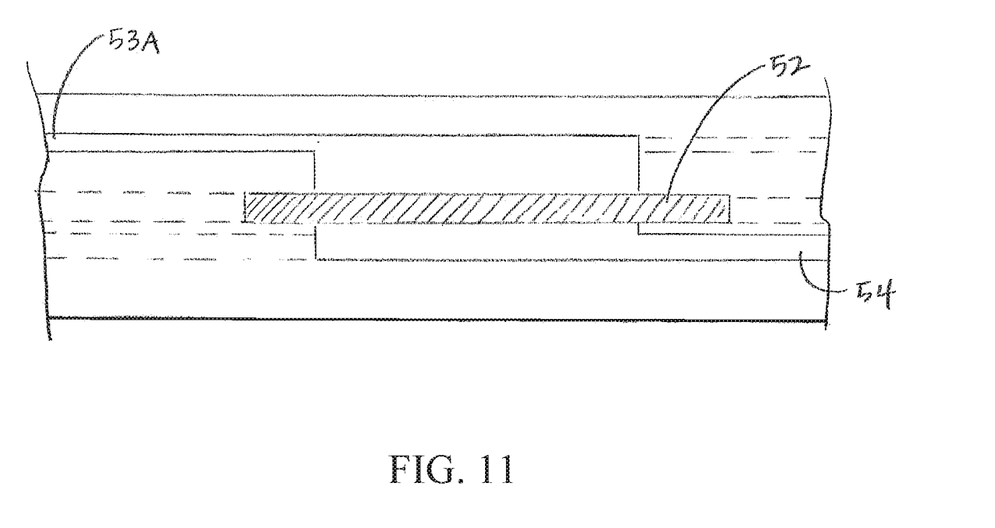
FIG. 11 shows a cross-sectional view taken along line 7-7 in FIG. 2 of a second control and delivery zone in the cartridge of FIG. 1, in accordance with an embodiment.

The gas permeable membranes 52 are provided at a depth within the housing, e.g., adjacent to and below the depth of the chambers 50, such as shown in FIG. 11, in accordance with an embodiment. Each gas permeable membrane 52 may receive and deliver atmospheric air into the housing. The gas permeable membranes 52 may be formed from a membrane or material that is configured to receive, pull, or deliver atmospheric air into the housing of the cartridge 100 while also being configured to prevent fluid(s) from entering into communication channels 54 that are connected to pump ports 56. In an embodiment, the membranes 52 are used to pull air to a certain pressure through and into chambers 50. In an embodiment, when the fluids reach the gas permeable membranes 52, it may be determined in any number of ways, e.g., it may be sensed using a detector, determined based on a known volume of the chambers 50, and/or based on a predetermined amount of time for applying negative pressure (suction or vacuum) to the fluid chambers 50 for metering the fluids. FIG. 11 shows a cross section of a portion of the second control and delivery zone 16 in the cartridge 100, in accordance with an embodiment. The gas permeable membrane 52 may be provided in the form of a piece of adhesive film that is sandwiched between layers and provided in a pocket, for example. Fluid may be pulled to the top surface until it is whetted, providing the hard stop for the fluids pulled into the chambers 50.

Extending from the gas permeable membrane 52 are communication channels 54 that are connected to a pump interface provided in the second delivery and control zone 16. In accordance with an embodiment, the channels 54 are provided at a depth within the housing that is below the membranes 52 and chambers 50 (see, e.g., FIG. 11). As schematically depicted in FIG. 2, the pump interface includes a number of pump ports 56 that connect to one or more pumps (provided offline of the cartridge 100). In the general context, each of the pump ports 56 are associated with a pressure switch. The pumps are controlled or switched to apply positive pressure or negative pressure (suction or vacuum) to the pump ports 56, or no pressure at all, and thus apply such pressure the fluid metering chambers 50 and channels in the valve array zones 40. In cooperation with these zones 40, based the position and switching of the pumps and valves therein, then, fluids may be moved throughout the cartridge 100 and mixed. Such details are explained later.

Figure 5:
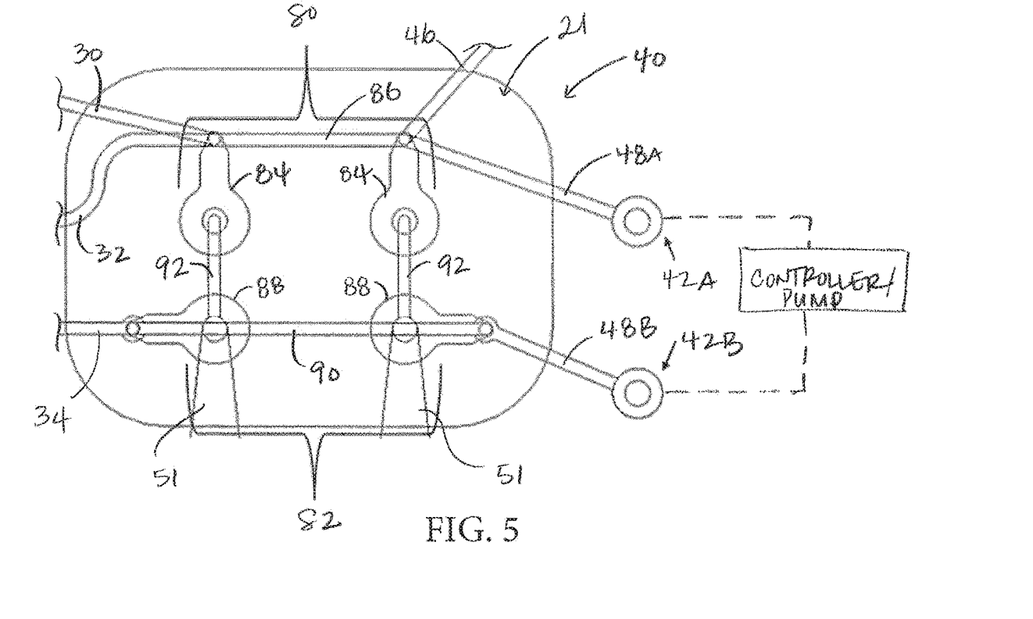
FIG. 5 is a detailed view of a valve array provided in the cartridge of FIG. 1, in accordance with an embodiment.

Turning back to the valve array zones 40, in accordance with an embodiment, each valve array zone 40 comprises a first set 80 of valves and a second set 82 of valves, shown in greater detail in FIG. 5, which are controlled using a valve actuation interface 42 (or controller interface). The sets 80 and 82 may be formed in the elastomeric material 21, e.g., via laser cutting or molding, for example, in the form of elastomeric deflection portions. Although the sets 80 and 82 are shown in the Figures to include two valves each that are positioned on either side of a longitudinal axis or centerline A-A (four valves for each set, i.e., a total of eight valves), it should be noted that, in one embodiment, a single valve for each set may be provided (i.e., a total of four valves). Additionally, the use of the term "set" is not intended to be limiting to the same type of valve. In an embodiment, a first valve 80 and a second valve 82 may be referred to as a "set."

The valve actuation interface 42 includes ports and control channels for selectively opening and closing the sets of valves in the zones 40. Specifically, FIG. 5 shows a detailed view of one embodiment of the valve array zone 40 provided on the right side of the cartridge 100, with valve actuation interface 42 connected thereto. However, it should be understood that the valve array zone 40 on the left side of the cartridge 100 is substantially a mirror image of the valves on the right side, as depicted by the use of similar reference numerals in the drawings. Additionally, the location of the valve actuation interface 42 is not limited to what is illustrated in the drawings. In one embodiment, the valve actuation interface 42 may be provided on an opposite (left) side of the cartridge 100. In another embodiment, an interface 42 may be provided on both sides of the cartridge 100.

The first set 80 of valves in each zone 40 may include two valves 84 that may be fluidly connected together via first channel 86, in accordance with an embodiment. Alternatively, in an embodiment, one valve 84 may be provided on either side of the centerline A-A. This first channel 86 may also be connected to one of the branch portions 30 for fluid communication therewith (i.e., to receive separated plasma). In another embodiment, branch portion 30 may be directly connected to a pocket associated with the valve 84. The second set 82 of valves in each zone 40 may include two valves 88 that are fluidly connected together via second channel 90, in accordance with an embodiment. Alternatively, in an embodiment, one valve 88 may be provided on either side of the centerline A-A. Additionally, as seen in FIG. 2, for example, a connecting channel 32 may extend between the first sets 80 of valves in the zones 40 on either side of the centerline A-A to communicatively and fluidly connect the valves 84 on the two sides. Connecting channel 32 may deliver pressurized air to each valve 84 provided in the cartridge 100, for example. Similarly, a connecting channel 34 may extend between the second sets 82 of valves for communicatively and fluidly connecting the valves 88 in the zones 40, on either side of the centerline A-A. Connecting channel 34 also allows communication between metering chambers 50 and mixing channels 58, when valves 88 are in an open state. Connecting channel 34 may be in fluid communication with second channel 90 and metering chamber 50 via transition sections 51, as noted below. Further, metering channels 92 may be provided between valves 84 and fluid metering channels 50. As shown in the detailed view of FIG. 5, the metering channels 92 connect to transition sections 51 that are connected to or part of the metering channels 50.

As seen in FIG. 5, in accordance with an embodiment, also connected to first channel 86 may be a control channel 48A. Control channel 48A is connected to a control port 42A of the valve actuation interface 42. Connected to second channel 90 may be a control channel 48B that is connected to a control port 42B in the valve actuation interface 42. The control ports 42A, 42B of the valve actuation interface 42 are connected to one or more offline pumps or controllers (schematically depicted in FIG. 5) that are designed to open and close each of the valves 84 and/or 88, as needed, during processing of a test sample.

In accordance with an embodiment, the opening and closing of each of these valves 84, 88 is mediated by use of positive and negative pressure gradients generated offline using the controller(s) and a connection to the ports of the valve actuation interface 42. In one embodiment, each of the valves 84 and 88 may be formed from a flexible elastomer or deflection portion that, based on an amount of force or pressure applied thereto, moves a state of each valve between its open and closed positions. In accordance with an embodiment, each valve 84 and 88 may be configured to be in a normally open state or open position, at rest. Upon application of an amount of pressure (e.g., pressurized air), the noted valve may be moved to a closed position.

Figure 6:
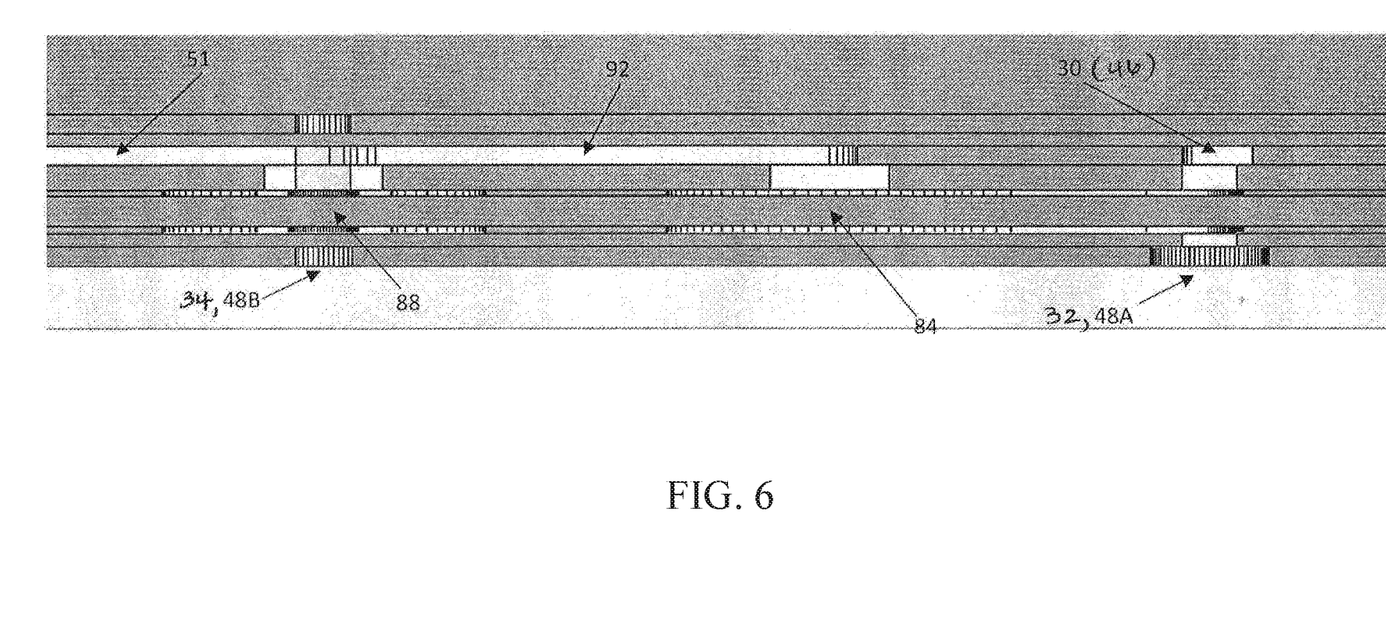
FIG. 6 shows a cross-sectional view taken along line 6-6 in FIG. 2 of the valve array and control zone in the cartridge of FIG. 1, in accordance with an embodiment.
Figure 7:
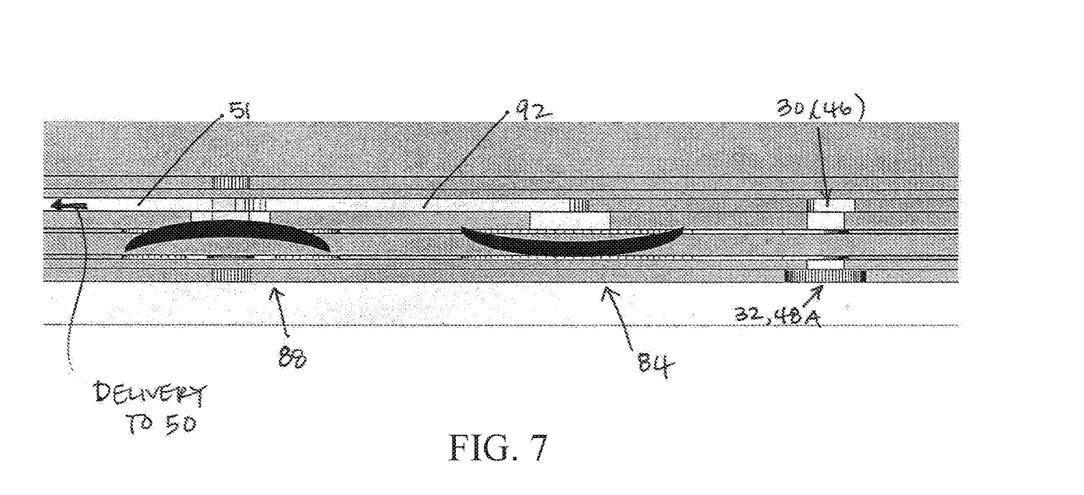
FIG. 7 is a schematic of the cross-section of FIG. 6 illustrating positioning of the valves in a first state.
Figure 9:
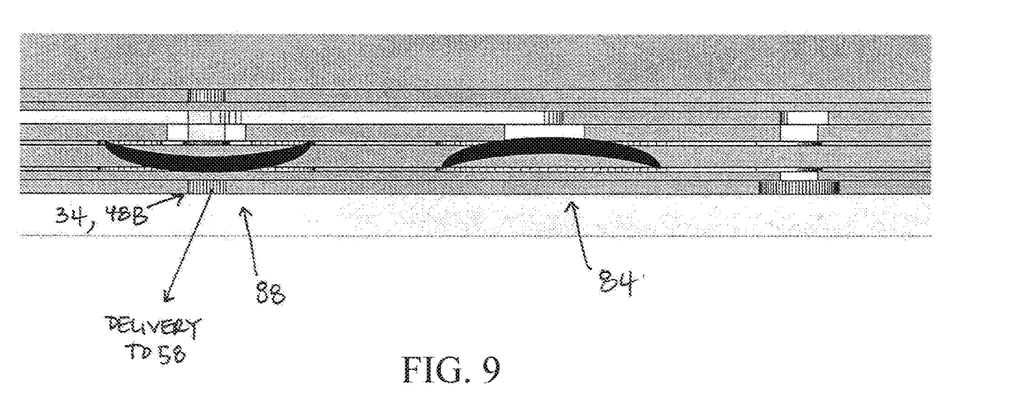
FIG. 9 is a schematic of the cross-section of FIG. 6 illustrating positioning of the valves in a second state.

As shown in FIGS. 6, 7, and 9, each of the channels connecting to the valves 84, 88 is positioned at a depth within the body or housing of the cartridge 100. In an embodiment, the channels are formed within layers of the housing as it is manufactured. The positioning of the channels at different depths allows fluid to flow therethrough without interfering with other parts of the housing.

Figure 8:
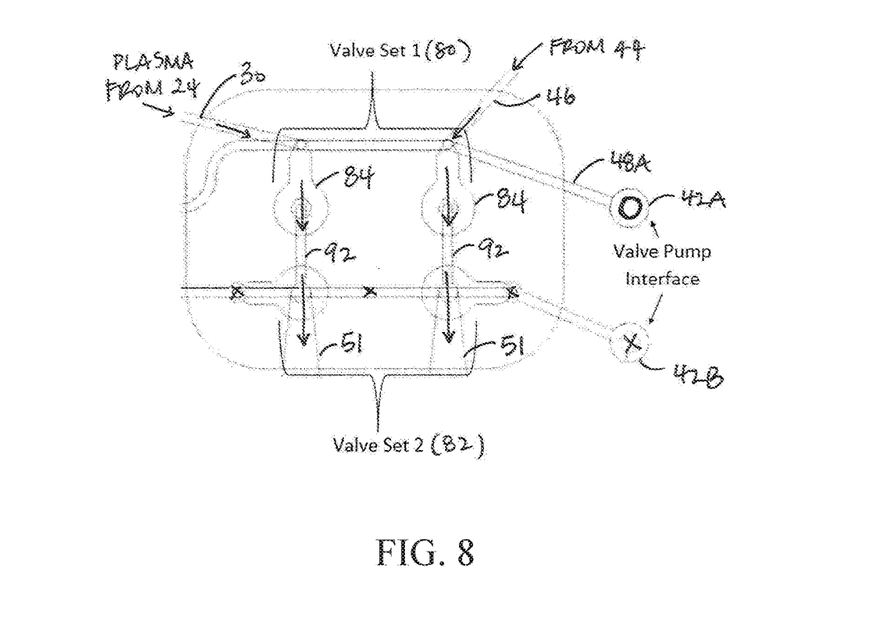
FIG. 8 is a detailed view of the valve array showing flow within channels in the first state.
Figure 10:
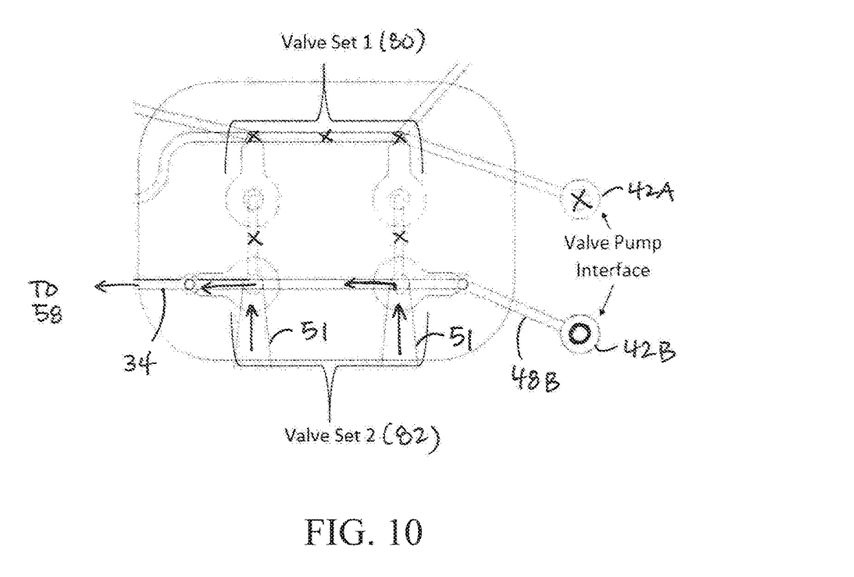
FIG. 10 is a detailed view of the valve array showing flow within channels in the second state.

For example, FIG. 6 shows a cross section take in the valve array and control zone 12, showing the connection and positioning of the aforementioned channels 30, 32, 34, 92, 51 (50), 48A, and 48B, and valves 84, 88 and their positioning within the housing (some of the lines illustrate exemplary layers that may be used to form the housing). The depths at which channels and valves are illustrated are exemplary only. Based on the state of the valves, the channels may be connected or blocked. That is, flow through the channels may be controlled based on movement of the elastomeric deflection portions relative to the channels, as activated by application of pressure via interface 42. For example, as shown in FIG. 7, in a first state, each valve 84 may be open, while valve 88 is closed (e.g., via pressurized air being applied to control channel 48B). Such features are represented here by arcs, to illustrate that the open valve 84 allows for fluid communication from 30 and 46, and in channel 34, through valve 84 and channel 92, and into chamber 50 via transition section 51. Fluid flow is blocked from delivery through valve 88 and into channel 34. FIG. 8 (which is also referenced below) schematically illustrates, for example, the movement of fluid in the first state of FIG. 7. In a second state, shown in FIG. 9, each valve 88 may be open, while valve 84 is closed (e.g., via pressurized air being applied to control channel 48A). Again, the positioning of the arcs illustrates that the open valve 88 allows for fluid communication from chamber 50 via transition section 51, through valve 88 and channel 90, and into mixing channel 58. Fluid flow is blocked from delivery through valve 84 and through channel 32. FIG. 10 (which is also referenced below) schematically illustrates, for example, the movement of fluid in the second state of FIG. 9.

As such, when each valve 88 is closed, fluid(s) are directed towards channels 50. When each valve 88 is open, fluid is directed towards mixing channels 58.

In one embodiment, the amount of pressure/pressurized air applied to the interface 42 to move valve(s) 84, 88 between their open and closed positions may be within a range of approximately 2.0 psi to approximately 10.0 psi. In one embodiment, approximately 5.0 psi may be applied to the interface 42 to move the valve(s) between positions, i.e., from an open state to a closed state. Generally, the required amount of pressure for setting the state of the valves is small.

In one embodiment, such as shown in the Figures, the valve actuation interface 42 (i.e., control channels 48A, 48B and control ports 42A, 42B) may be provided on one side of the cartridge 100 for controlling both sets of valves in the valve array zone 40. Accordingly, the fluid connection via connecting channels 32 and/or 34 allows for controlling assays on both (longitudinal) sides of the cartridge 100. Nonetheless, it should be noted that the illustrated embodiment is not intended to be limiting. In another embodiment, the channels 48A, 48B and control ports 42A, 42B may be provided on an opposite (left) side of the cartridge 100 and connected to the valves on the left side of that zone 40. In yet another embodiment, control channels 48A, 48B and control ports 42A, 42B may be provided on both sides of the cartridge 100.

In an embodiment, connected to each metering chamber 50 is a pump port 56 configured to selectively draw and deliver pressurized fluid to (into) and from the housing. In another embodiment, a pump port 56 may connect to more than one chamber 50. The pump ports 56 may be a part of a pump interface that is provided in a lower portion of the housing. The pump ports 56 may be positioned relative to and accessed via the top surface 18, the bottom surface 20, or a combination thereof. In another embodiment, the pump ports 56 may be positioned on a side of the housing. The pump connected to the pump ports 56 at this interface may be a different pump or a similar pump connected at the valve interface 42. The pump ports 56 may be used to move and mix fluids throughout the channels in the housing of cartridge 100. Depending on the state (open or closed) of the valves and the pump(s) connected at pump ports 56, the metering channels 92 allow for either or both of the test sample (plasma) and reagent(s) to be pulled into fluid metering chambers 50 and/or pushed from said metering chambers 50 into mixing channels 58. Negative (suction or vacuum) pressure may be applied by pump to the pump ports 56 to draw fluids (plasma, reagent) through the valves in zone(s) 40, for example. Positive pressure (e.g., in the form of a pressurized fluid such as pressurized air) may be applied to pump ports 56 to deliver fluids from the metering chamber(s) 50 to mixing channels 58.

In accordance with an embodiment, the fluid metering chambers 50 may also be fluidly connected to the second channel 90 via a transition section 51 provided at its top end, as generally represented in FIG. 5, for example. In accordance with an embodiment, a corresponding transition section 53, shown in FIG. 2, for example, along with a fluid line 53*a* may also be provided at a bottom end of each fluid metering chamber 50 near each gas permeable membrane 52. Transition section 51 is formed such that its width expands from a reduced width (near the interface 42) to a width similar to that of the top/entrance of the chamber 50, and transition section 53 reduces in its width from the bottom/exit of the chamber 50 to a reduced width at its relative fluid line 53*a*. The size and shape of the transition sections 51, 53 are formed in this manner in order to reduce and/or prevent air bubbles from forming in the chambers 50. They further assist in providing smoother fluid flow when fluid is moved through the chamber 50 (explained later).

Figure 3:
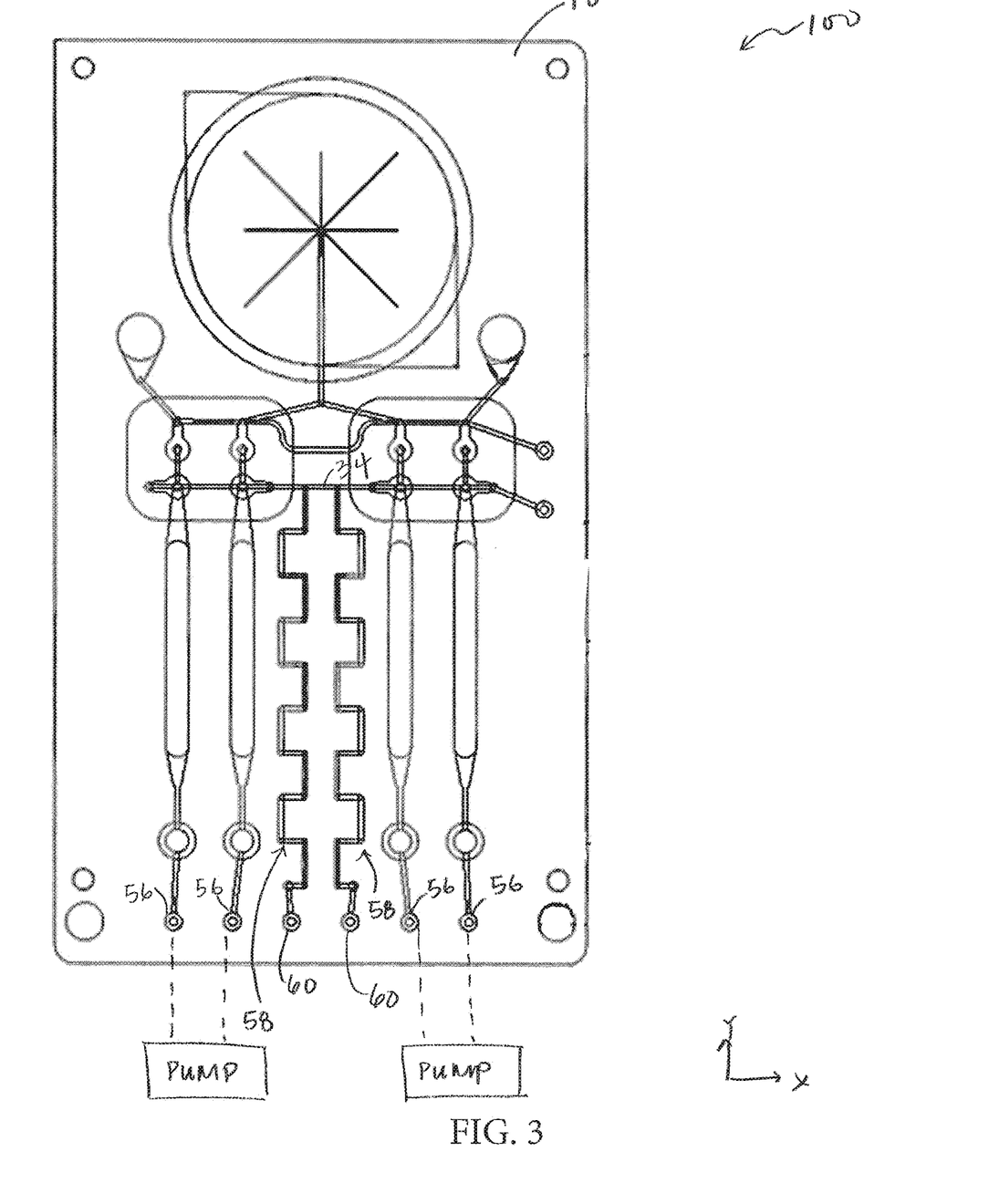
Figure 4:
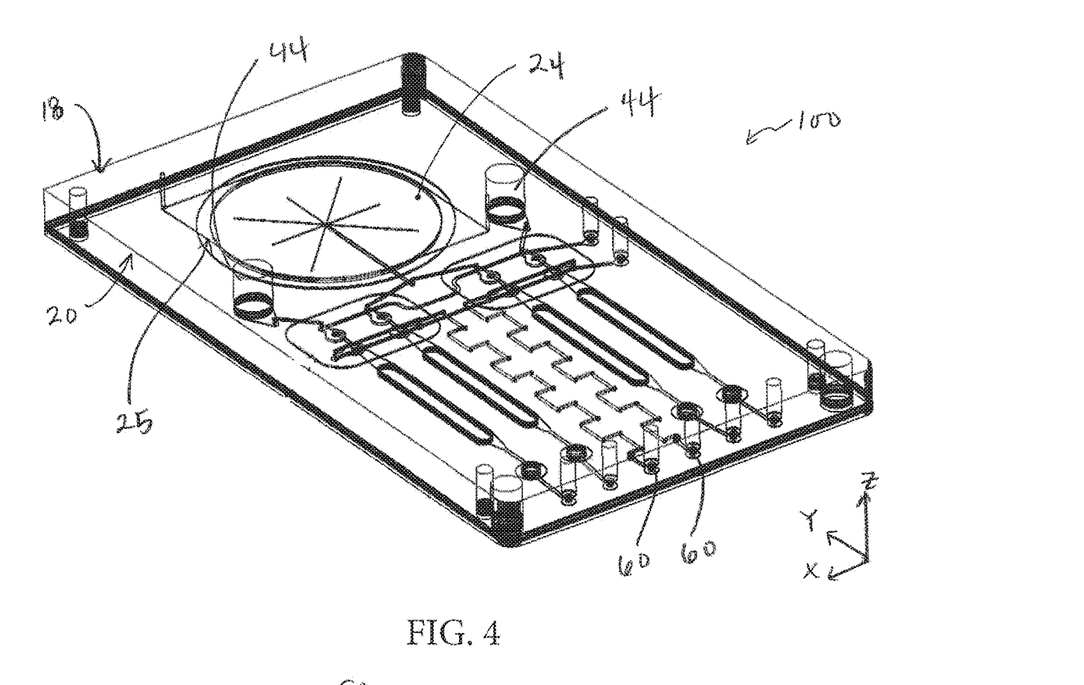
FIG. 4 is a bottom angled view of the cartridge of FIGS. 2 and 3.

FIG. 3 shows the above mentioned mixing channels 58 in greater detail. Each of these channels 58 may be used to mix or further mix the metered patient (plasma) sample and reagent that is drawn into the chambers 50, which will be further explained below. The mixing channels may be designed to mix or further mix the plasma and reagent into a substantially homogeneous or homogeneous mixture, for output and use in testing. The mixing channels 58 may be provided to extend longitudinally from near or adjacent to the valve array and control zone 12, into the mixing zone 14, and end at the second control and delivery zone 16 of the cartridge. In accordance with an embodiment, two mixing channels 58 are provided in the housing at a depth below the chambers 50. The positioning of each mixing channel 58 may be such that it is provided adjacent to or near a middle or centerline A-A thereof, in accordance with one embodiment. For example, as shown in the Figures, when two mixing channels 58 are provided, each channel may be provided on an opposite side of the longitudinal axis or centerline A-A. One mixing channel 58 may be associated with two metering chambers 50, in accordance with an embodiment.

Each of the mixing channels 58 may be connected at a first (input) end to connecting channel 34 and to a sensor delivery output port 60 at a second (output) end. In accordance with an embodiment; each of the channels 58 may have a stepped configuration between its ends that includes portions that extend longitudinally (or vertically, or in the Y-direction) and portions that extend laterally (or horizontally, or in the X-direction) in the housing of the cartridge 100. This stepped configuration enables the fluids to be moved through planes and induce turbulence in the fluids via its bends, to thereby blend and/or mix the fluids thoroughly into a substantially homogeneous or homogeneous mixture.

The sensor delivery output ports 60 may be referred to herein as "output ports" at a sensor delivery interface of the cartridge 100, designed for delivering the mixed sample and reagent mixture from the cartridge 100 to one or more sensors provided in a system or device. As shown, the output ports 60 may be provided in a lower portion of the housing. Output delivery via output ports 60 is controlled using the valves 84, 88, pump ports 56, controller(s) and/or pump(s), as described with reference to FIG. 12 below.

The output ports 60 may be positioned relative to and accessed via the top surface 18, the bottom surface 20, or a combination thereof. In another embodiment, the output ports 60 may be positioned on a side of the housing. In one embodiment, the sensor delivery output ports 60 may be configured to output the fluid mixture through the bottom surface 20 of the cartridge, and thus the output ports 60 may be associated with or positioned adjacent to a sensor provided underneath the cartridge 100. In another embodiment, the sensor delivery output ports 60 may be configured to output the fluid mixture through the top surface 18 of the cartridge, and thus the output ports 60 may be associated with or positioned adjacent to a sensor provided above the cartridge 100. For example, the sensor(s) may be provided on a hand held mechanism or system. The output ports 60 may be positioned on a location of the cartridge 100 that cooperates and meets an inlet(s) of sensor(s) on such a device, so that the sensor(s) can detect and produce an output reading from the substantially homogeneous mixture that is output from the housing. The location of the output ports 60 is not intended to be limiting.

In accordance with an embodiment, the disclosed cartridge 100 is configured for use with a system or device designed to provide technicians with convenient and fast analyte detection in a single process. The device may detect a level of analyte within an input blood sample, for example. In one embodiment, the system or device may be a handheld or mobile device or system configured to connect with or receive the cartridge 100. For example, the card may interface with a handheld system via a face seal using o-rings that are clamped down to the top of the card. This seal permits a negative pressure to be achieved that facilitates fluid movement throughout the card, as described below with reference to FIG. 12 and method 200, in accordance with one embodiment. The mixture from cartridge 100 may be input into the device or sensor, and the presence of multiple biomarkers may be detected by capturing proteins from the mixture and quantifying their presence based on magnetic field detection. In an embodiment, the system or device 200 may employ one or more sensors 64 configured to detect analytes in a mixture/sample by displacing competing analytes labeled with magnetic nanoparticles and sensing a change in the magnetic field created by the magnetic nanoparticles via a magnetic (field) sensor, e.g., a giant magnetoresistance (GMR) sensor or other MR sensors (e.g., AMR, TGMR, etc.). One or more sensors or an array of magnetic sensors may be formed on a chip, for example, so that multiple antigenic analytes are detected with specificity within the sample. The device may include an interface and a display for prompting a user to input and/or connect the cartridge with the device and/or sample, for example. The device may include the controller(s) and/or pump(s) used to move and mix fluids in the cartridge 100. In accordance with an embodiment, in combination with the disclosed cartridge 100, the device may process, detect, analyze, and generate a report of the results, e.g., regarding multiple biomarkers, e.g., five cardiac biomarkers, using sensor (GMR) technology, and further display the biomarker results, as part of one process.

Figure 12:
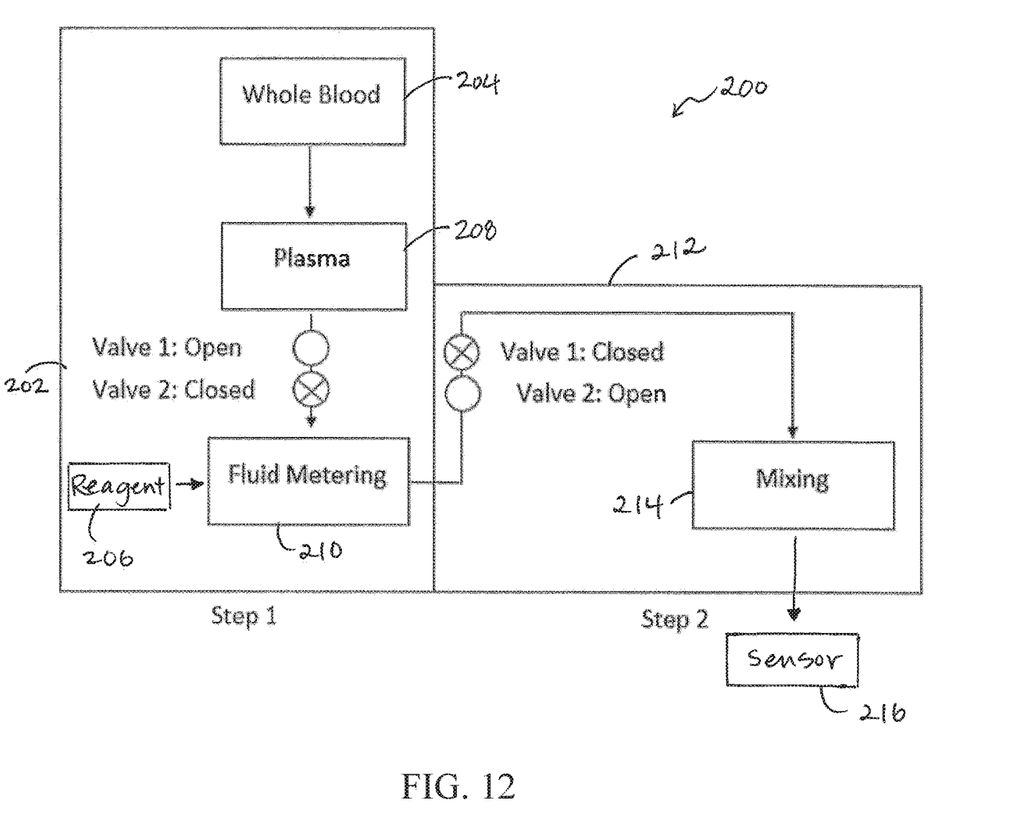
FIG. 12 is a flow chart of a method of using the cartridge of FIG. 1.

FIG. 12 is a flow chart of a method 200 of using the cartridge 100, e.g., with a handheld system or device or another offline device or system that has controllers) and/or pump(s) and sensor(s) connected to each of the cartridge interfaces (e.g., interface 42, pump interface and pump ports 56, and output ports 60 at the sensor output interface). For explanatory purposes only, reference to a single pump (or controller) is noted here, but is not meant to be limiting. In an embodiment, in a first state, the first set of valves, valves 84, are in an open position, while the second set of valves, valves 88, are in a closed position. In a second state, the first set of valves (84) are in a closed position, while the second set of valves (88) are in an open position.

In accordance with an embodiment, the method of using the herein disclosed cartridge 100 to mix a test sample (blood) and reagent follows steps of method 200, The valve states of the valves 84 and 88 are initially set as follows, as shown at 202: pump is attached to the valve pump interface 42 and controlled and configured to apply positive pressure through interface 42 via port 42B and 48B to second channel 90, including through channel 34 to the channel 90 on an opposite side of the centerline AA, such that all valves 88 (Valve are moved to a closed position. In an embodiment, no pressure is applied to first channel 86 and channel 32, and thus all valves 84 (Valve 1) remain in an at rest/default state, i.e., an open position. In another embodiment, the pump may be controlled to position the valves 84 in an open state. A whole blood sample is input or injected at 204, e.g., into the injection port 22 of the cartridge. Reagent is stored in the cartridge 100, as shown at 206, and ready for mixing. As described in greater detail above, the reagent may be stored or added to the cartridge 100, e.g., in section 44. Plasma is separated at 208 from the input blood sample, e.g., using filtration membrane 24. At the pump interface at a lower end of the housing, a pump is also attached to the pump ports 56. Negative (suction or vacuum) pressure may be applied by pump to the pump ports 56, thereby pulling the separated plasma and reagent into the fluid metering chambers, as shown at 210. For example, the vacuum pressure pulls plasma through the branches 30 into the first channel 86, through valves 84 and metering channels 92, and into fluid chambers 50. At the same time, reagent is pulled through 46, through valves 84 and metering channels 92 and into fluid chambers 50 (see, e.g., FIG. 8). This action allows the two fluids to be forced into the mixing region in a 1:1 ratio. Both fluids are metered or pulled until they reach the gas permeable membranes 52, for sample.

After the metering at 210, the valve states in the zones 40 are switched, as shown at 212. The pump is reversed and controlled to apply positive pressure through interface 42 via port 42A and control channel 48A to first channel 86, including through channel 32 to the channel 86 on an opposite side of the centerline AA, such that all valves 84 (Valve 1) are moved to a closed position. In an embodiment, no pressure is applied to second channel 90 and channel 34, and thus all valves 88 (Valve 2) remain in an at rest/default state, i.e., an open position. In another embodiment, the pump may be controlled to position the valves 88 in an open state. The pump may also be controlled to apply positive pressure at the pump interface through pump ports 56, channels 54 and membranes 52, such that it moves or pushes the metered fluids (i.e., plasma and reagent) to and through second channels 90, into channel 34, and then into mixing channels 58 (see, e.g., FIG. 10). The continuous application of pressure through ports allows for mixing, as indicated at 214, of the fluids as they move through (e.g., the stepped configuration of) the mixing channels 58, to form a substantially homogenous or homogeneous mixture of the plasma and reagent. The mixed fluids exit or are output from the cartridge 100, e.g., via output ports 60, to a sensor that is part of the handheld system or device, as represented at 216. The sensor uses the mixed, homogeneous fluid to sense or detect biomarkers in the sample.

At the end of the method, although not depicted in FIG. 12, the cartridge 100 may be connected to the system or device with the offline sensor(s) such that the output ports 60 are configured to deliver the mixture of fluids to the sensor(s), such that the multiple biomarker reading may be performed and output (e.g., via the display) to the user.

In an embodiment, a test sample of approximately 100 mL to approximately 500 mL (inclusive) of blood is configured to be injected into the injection port 22. In an embodiment, a test sample of approximately 300 mL of blood is configured to be injected into the injection port 22. In an embodiment, the blood filtration membrane 24 is configured to yield approximately 50 mL to approximately 250 mL of plasma. In an embodiment, the blood filtration membrane 24 is configured to yield approximately 100 mL of plasma.

In accordance with an embodiment, approximately 50-100 ml of reagent may be provided in the reagent injection sections 44 and/or used in the cartridge (e.g., during metering as described in the method 200).

In accordance with an embodiment, the total processing time from injection to output (out to sensor) of the method 200 may take approximately fifteen to twenty minutes, depending on the pump design and settings. However, the processing time may be altered and is not meant to be limiting.

In an embodiment, the cartridge 100 may be fabricated by stacking and laminating different types and layers of laser cut, polymer materials, to produce the described channel geometries and shapes shown in the Figures. In addition to these layers, the gas permeable membrane 52, blood filtration membrane 24, and/or elastomer material over zones 40 may also be laser cut and placed in designated regions of the cartridge to provide the required functionality. However, as noted throughout this disclosure, any number of manufacturing methods and/or materials may be used to manufacture the cartridge 100.

The herein disclosed cartridge 100 uses interfaces, valves, and channels to allow for autonomous metering and mixture of (stored) reagents with a patient blood sample that is input therein as part of a single application or process. The method 200 of using the disclosed microfluidics cartridge 100 or card allows for a user to perform mixing of a sample as part of a single process, and analysis when used in conjunction with a device (sensor) or system, so that multiple biomarkers features in the sample may be detected. The metering of the fluids and subsequent mixing operations are controlled entirely by off-cartridge pump(s) and controller(s) that are connected to the cartridge, which allows for a complete automation of the assay process that previously required human technicians. The standardization of geometries and fluid movement also allows for a more stable platform, as more elements of the system are controlled.

Also, using this disposable point of care cartridge 100, a wider range of detection is possible while using a smaller amount of patient blood sample, without sacrificing speed in the production of results. For example, the disclosed assay cartridge design permits the detection of multiple biomarkers from a single sample, and thus facilitates multiplex analysis of target biomarkers from a single patient sample. In a particular embodiment, the disclosed cartridge 100 utilizes the patient blood sample for targeting multiple (e.g., five) biomarkers associated with cardiac distress.

Further, the structural features of the disclosed cartridge 100 permits multiple assays to run in parallel.

In accordance with an embodiment, the described valving and fluid metering strategies could be replicated and utilized in other cartridge designs as well. That is, the channels and/or elastometric features (deflection portions), along with use of a pump and/or controller for pneumatic movement and control via pressurized air, may be applied to other cartridge designs. Accordingly, the number and type of channels as shown in the Figures is not intended to be limited to the illustrated design.

The illustrated structural features shown in the Figures of this disclosure are not intended to be limiting. For example, the numbers of sets, valves, metering chambers, membranes, mixing channels, and/or ports are not intended to be limited with regards to those shown. In some embodiments, more channels may be provided. In some embodiments, less channels may be provided. The number of valves is also not intended to be limiting. In one embodiment, a valve set may be a first valve 84 and a second valve 88. Two valve sets may be provided in cartridge 100, in accordance with an embodiment. In another embodiment, four valve sets may be provided in cartridge 100.

Although the cartridge is described throughout as being used with a reagent and a patient or medical blood sample, it should be noted that the herein disclosed cartridge 100 is not limited to use with blood or solely in medical practices. Another fluids that may be separable and combined with a reagent or reactionary material may be employed in the herein disclosed cartridge for assaying.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. An assay cartridge for mixing a test sample and reagent for diagnostic purposes, the assay cartridge comprising:
 a housing having a top surface and a bottom surface and extending in a longitudinal direction of the assay cartridge;
 an injection port, provided on the top surface of the housing, for receiving the test sample;
 a filtration membrane provided in between the top surface and the bottom surface of the housing for filtering the test sample after injection into the injection port to produce a filtered test sample that is received in a receiving area in the housing;
 a reagent injection section for receipt of the reagent;
 a first set of valves provided in the housing comprising at least a first valve and a second valve, each of the first valve and the second valve comprising a deflection portion that is configured for movement between a first position and a second position;
 a sample delivery channel provided in the housing extending between the receiving area and the first set of valves and a reagent delivery channel extending between the reagent injection section and the first set of valves, for fluid communication therebetween;

at least one metering chamber provided in the housing for receiving the filtered test sample and the reagent therein via connections to the sample delivery channel and the reagent delivery channel, the at least one metering chamber extending a length along the longitudinal direction of the housing;

at least one pump port provided in the housing fluidly connected to the at least one metering chamber via a communication channel, the pump port configured to selectively draw and deliver pressurized fluid into the housing when connected to a pump;

a gas permeable membrane provided in the housing relatively below both the top surface of the housing and the at least one metering chamber, the gas permeable membrane being configured to receive and deliver atmospheric air into the at least one metering chamber while also being configured to prevent the filtered test sample and the reagent from entering into the communication channel, wherein the communication channel is provided at a depth within the housing below the top surface of the housing and below both the gas permeable membrane and the at least one metering chamber;

at least one mixing channel provided in the housing for mixing the filtered test sample and reagent into a substantially homogeneous mixture, the at least one mixing channel being connected to the at least one metering chamber via a connecting channel extending therebetween, and wherein fluid communication through the connecting channel is configured to be selectively limited based on positioning of the first and second valves; and at least one output port for delivering the homogeneous mixture from the at least one mixing channel and out of the housing, wherein the at least one mixing channel is connected at a first end to the connecting channel and at a second end to the at least one output port, and wherein the mixing channel comprises a stepped configuration between the first and second ends that includes alternating first portions and second portions, the first portions extending longitudinally in the longitudinal direction and the second portions extending laterally relative to the longitudinal axis of the housing, wherein, when the deflection portion of the first valve is provided in the first position and the deflection portion of the second valve is provided in the second position, fluid communication is established between the sample delivery channel and the reagent delivery channel and the at least one metering chamber, while fluid communication into connecting channel and the at least one mixing channel is blocked via the second valve, and wherein, when the deflection portion of the first valve is provided in the second position and the deflection portion of the second valve is provided in the first position, fluid communication established between the at least one metering chamber, the connecting channel, and into the at least one mixing channel, while fluid communication with the sample delivery channel and the reagent delivery channel is blocked via the first valve.

2. The assay cartridge according to claim 1, wherein the reagent injection section comprises a well.

3. The assay cartridge according to claim 2, wherein the well contains the reagent therein.

4. The assay cartridge according to claim 1, further comprising one or more control ports configured to deliver pressurized air to the first set of valves.

5. The assay cartridge according to claim 4, wherein each of the first and second valves comprises an elastomeric deflection portion configured for movement between the first and second positions via injection of pressurized air into the one or more control ports.

6. The assay cartridge according to claim 1, further comprising a vent port in the housing, wherein the vent port is open to atmosphere and configured to vent air from the housing.

7. The assay cartridge according to claim 1, further comprising:
a second set of valves provided in the housing comprising at least a third valve and a fourth valve, each of the third valve and the fourth valve comprising a deflection portion that is configured for movement between a first position and a second position.

8. The assay cartridge according to claim 7, further comprising one or more control ports configured to deliver pressurized air to the second set of valves.

9. The assay cartridge according to claim 8, wherein each of the third and fourth valves comprises an elastomeric deflection portion configured for movement between the first and second positions via injection of pressurized air into the one or more control ports.

10. The assay cartridge according to claim 7, further comprising:
an additional metering chamber provided in the housing for receiving the filtered test sample and the reagent therein via connections to the sample delivery channel and the reagent delivery channel;
a second pump port provided in the housing fluidly connected to the additional metering chamber via a second communication channel, the second pump port configured to selectively draw and deliver pressurized fluid into the housing when connected to the pump;
a second gas permeable membrane provided in the housing relatively below both the top surface of the housing and the additional metering chamber, the second gas permeable membrane being configured to receive and deliver atmospheric air into the additional metering chamber while also being configured to prevent the filtered test sample and the reagent from entering into the second communication channel, the second communication channel extending between the second gas permeable membrane and the second pump port, wherein the second communication channel is provided at a depth within the housing below the top surface of the housing and below both the second gas permeable membrane and the additional metering chamber;
an additional mixing channel provided in the housing for mixing the filtered test sample and reagent into a substantially homogeneous mixture, the additional mixing channel being connected to at least the additional metering chamber via a second connecting channel extending therebetween, and wherein fluid communication through the second connecting channel is configured to be selectively limited based on positioning of the third and fourth valves; and
an additional output port for delivering the homogeneous mixture from the additional mixing channel and out of the housing, wherein the additional mixing channel is connected at a first end to the second connecting channel and at a second end to the additional output port, and wherein the additional mixing channel comprises a stepped configuration between the first and second ends that includes alternating first portions and second portions, the first portions extending longitudinally in the longitudinal direction and the second portions extending laterally relative to the longitudinal axis of the housing, wherein, when the deflection portion of the third valve is provided in the first position and the deflection portion of the fourth valve is provided in the second position, fluid communication is established between the sample delivery channel and the reagent delivery channel and the additional metering chamber, while fluid communication into second connecting channel and the additional mixing channel is blocked via the fourth valve, wherein, when the deflection portion of the third valve is provided in the second position and the deflection portion of the fourth valve is provided in the first position, fluid communication established between the additional metering chamber, the second connecting channel, and into the additional mixing channel, while fluid communication with the sample delivery channel and the reagent delivery channel is blocked via the third valve, and wherein the additional metering chamber is parallel, in a lateral direction, to the at least one metering chamber and extending a length along the longitudinal direction of the housing.

11. The assay cartridge according to claim 10, wherein the first set of valves, the second set of valves, the at least one metering chamber, and the additional metering chamber are provided on a same side of a longitudinal axis of the housing.

12. The assay cartridge according to claim 10, wherein the first set of valves and the at least one metering chamber are provided on a first side of a longitudinal axis of the housing, and wherein the second set of valves and the additional metering chamber are provided on a second side of the longitudinal axis of the housing.

13. The assay cartridge according to claim 1, wherein a transition section is provided between the at least one metering chamber and the at least one mixing channel, the transition section having a first width at a first end closest to the at least one mixing channel and a second width at a second end closest to the at least one metering chamber, the first width being smaller than the second width.

* * * * *